(12) United States Patent
Ganesan et al.

(10) Patent No.: US 6,326,784 B1
(45) Date of Patent: Dec. 4, 2001

(54) NUCLEAR MAGNETIC RESONANCE LOGGING WITH AZIMUTHAL RESOLUTION USING GRADIENT COILS

(75) Inventors: Krishnamurthy Ganesan; Steven F. Crary, both of Sugar Land; Ralf Heidler, Stafford; Bruno Luong, Stafford; Peter Speier, Stafford, all of TX (US)

(73) Assignee: Schlumberger Technology Corporation, Houston, TX (US)

( * ) Notice: Subject to any disclaimer, the term of this patent is extended or adjusted under 35 U.S.C. 154(b) by 0 days.

(21) Appl. No.: 09/186,951

(22) Filed: Nov. 5, 1998

(51) Int. Cl.$^7$ ..................................................... G01V 3/00
(52) U.S. Cl. ............................................................. 324/303
(58) Field of Search .................................. 324/303, 300, 324/306, 307, 309, 318, 322

(56) References Cited

U.S. PATENT DOCUMENTS

| | | |
|---|---|---|
| 4,717,878 | 1/1988 | Taicher et al. . |
| 4,719,423 * | 1/1988 | Vinegar et al. ........................ 324/303 |
| 5,055,787 | 10/1991 | Kleinberg et al. . |
| 5,212,447 | 5/1993 | Paltiel . |
| 5,278,501 * | 1/1994 | Guifoyle ............................... 324/303 |
| 5,280,243 | 1/1994 | Miller . |
| 5,473,158 | 12/1995 | Holenka et al. . |
| 5,757,186 | 5/1998 | Taicher et al. . |
| 5,796,252 | 8/1998 | Kleinberg et al. . |

FOREIGN PATENT DOCUMENTS

WO 98/43064   10/1998  (WO) .

OTHER PUBLICATIONS

R. S. Dembo and U. Tulowitzki, "On the Minimization of Quadratic Functions Subject to Box Constraints," Yale Univ. School of Organization and Management, SOM Working Paper Series B #71, New Haven (1983).

* cited by examiner

*Primary Examiner*—Louis Arana
(74) *Attorney, Agent, or Firm*—John J. Ryberg; Brigitte L. Jeffery

(57) ABSTRACT

The present invention relates generally to an apparatus and method for obtaining an azimuthally resolved nuclear magnetic resonance measurement of an earth formation traversed by a borehole. The measurement can be made while drilling or using a wireline tool. At least one gradient coil is positioned circumferentially around the tool. A magnetic field is produced by the coil in a region of the formation facing the coil. The magnetic field is substantially parallel to the static magnetic field produced by a pair of permanent magnets which form a part of the tool. The additional field causes an additional phase shift for spins located in the region so that the spins subjected to the additional field do not form a spin-echo.

139 Claims, 8 Drawing Sheets

NUCLEAR MAGNETIC RESONANCE LOGGING WITH AZIMUTHAL RESOLUTION USING GRADIENT COILS

FIELD OF THE INVENTION

This invention relates to the field of well logging and, more particularly, to a method and apparatus for determining nuclear magnetic resonance logging characteristics of earth formations surrounding a borehole, as a function of angular position about the borehole, either during the drilling of the borehole (using an MWD or LWD device) or after drilling (using a wireline tool).

BACKGROUND OF THE INVENTION

Borehole nuclear magnetic resonance measurements provide different types of information about a reservoir. First, the measurements provide an indication of the amount of fluid in the formation. Second, the measurements present details about whether the fluid is bound by the formation rock or unbound and freely producible. Finally, the measurements can be used to identify the type of fluid—water, gas, or oil.

One approach to obtaining nuclear magnetic resonance measurements employs a locally generated static magnetic field, $B_0$, which may be produced by one or more permanent magnets or electromagnets, and an oscillating magnetic field, $B_1$, which may be produced by one or more RF antennas, to excite and detect nuclear magnetic resonance properties to determine porosity, free fluid ratio, and permeability of a formation. See U.S. Pat. No. 4,717,878 issued to Taicher et al. and U.S. Pat. No. 5,055,787 issued to Kleinberg et al. Nuclear spins align with the applied field $B_0$ with a time constant of $T_1$ generating a net nuclear magnetization. The angle between the nuclear magnetization and the applied field can be changed by applying an RF field, $B_1$, perpendicular to the static field $B_0$. The frequency of the RF field is equal to the Larmor frequency given by $\omega_0 = \gamma B_0$ where $\gamma$ is the gyromagnetic ratio. After application of an RF pulse, the magnetization begins to precess around $B_0$ and produces a detectable signal in the antenna.

Another approach to obtaining nuclear magnetic resonance measurements employs a locally generated static magnetic field, $B_0$, which may be produced by one or more permanent magnets or electromagnets, and an azimuthally-oriented oscillating magnetic field, $B_1$, which may be produced by one or more RF antenna segments that transmit and/or receive from different circumferential sectors of the logging device. See U.S. patent application Ser. Nos. 08/880,343 and 09/094,201 assigned to Schlumberger Technology Corporation. Typical long echo trains (~600 spin-echoes) are unobtainable with a rotating azimuthal antenna. Since the antenna is only properly positioned in the measurement direction during a short time, the signal decays faster due to rotation of the tool than it would due to formation properties alone.

U.S. Pat. No. 5,796,252 issued to Kleinberg et al. describes a nuclear magnetic logging device which includes permanent magnets, an RF antenna, and a coil for generating a magnetic field gradient. The technique described in the '252 patent utilizes pulsed magnetic field gradients to obtain information regarding diffusion properties of the formation fluids. If internal gradients are present in the formation, a pulse sequence is applied to reduce or substantially eliminate the effect of internal gradients in the formation. The '252 patent does not identify a method for using the coil to obtain an azimuthal NMR measurement.

U.S. Pat. No. 5,212,447 issued to Zvi Paltiel describes a nuclear magnetic logging device which includes permanent magnets and an RF antenna coil. The '447 patent requires a magnetic field gradient coil to determine a diffusion coefficient, i.e., the rate at which molecules of a material randomly travel within the bulk of the same material. The '447 patent employs the diffusion coefficient to determine at least one of the following petrophysical parameters: water/hydrocarbon discrimination, water and hydrocarbon saturation levels, permeability, pore size and pore size distribution, oil viscosity, a measure of the average increase in electrical resistance due to the formation tortuosity, and q-space imaging of the formation. The '447 patent does not identify a method for using the coil to obtain an azimuthal NMR measurement.

A primary object of this invention is to obtain an azimuthal NMR measurement. This measurement may be used to determine formation characteristics such as porosity, bound fluid volume, $T_2$, $T_1$, and permeability. Being able to measure the azimuthal variation of these characteristics is useful for interpreting heterogeneous formations and performing geologically based steering in deviated or horizontal boreholes.

Another object of the invention is to improve the vertical resolution of the tool using at least one gradient coil.

SUMMARY OF THE INVENTION

The above disadvantages of the prior art are overcome by means of the subject invention for an apparatus and method for determining nuclear magnetic resonance logging characteristics of earth formations surrounding a borehole, as a function of angular position about the borehole. The subject invention also performs azimuthal magnetic resonance imaging. A wireline or logging-while-drilling apparatus within a borehole traversing an earth formation determines a formation characteristic by obtaining a nuclear magnetic resonance measurement from a region of investigation. The apparatus includes a means for producing a static magnetic field, $B_0$. An RF antenna produces an oscillating field, $B_1$, in the same region of the formation as the static magnetic field to obtain the NMR measurement. The apparatus includes at least one gradient coil. The magnetic field produced by the gradient coil is substantially parallel to the static magnetic field, $B_0$.

When a current pulse is applied to the gradient coil, the spins in a portion of the investigation region will either completely or incompletely dephase. The geometry of the gradient coil determines whether the spins experience radial, azimuthal, or axial dephasing. For complete dephasing, the gradient field will alter the phase of spins in the portion of the investigation region by spatially varying the magnetic field strength so that a net magnetization within the section is zero. For incomplete dephasing, the gradient field will alter the phase of spins in the portion of the investigation region so that a net magnetization over the portion is non-zero and has a different phase than the net magnetization in the remaining portion of the investigation region.

A cross-section of the formation is partitioned to form either a plurality of angular distance segments, axial segments, or radial segments around the borehole. In addition, a radial partitioning of the borehole is described. A pulse sequence is applied to the formation under investigation. The pulse sequence comprises a symmetric phase alternated pulse sequence, i.e., a measurement without using the gradient coils, and/or a gradient phase alternated pulse sequence, i.e., a measurement using the gradient coils. The gradient coils dephase spins in at least of the segments. In one embodiment, an azimuthal measurement is created by subtracting the gradient measurement from the symmetric measurement. In a second embodiment, the azimuthal measurement is created by combining different single quadrant spoiling measurements. In a third embodiment, a plurality of azimuthal bins are defined and each NMR measurement is added to the content of the buffer associated with the bin in which the measurement was taken.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

In the drawings.

DETAILED DESCRIPTION OF THE PREFERRED EMBODIMENTS

Figure 1:
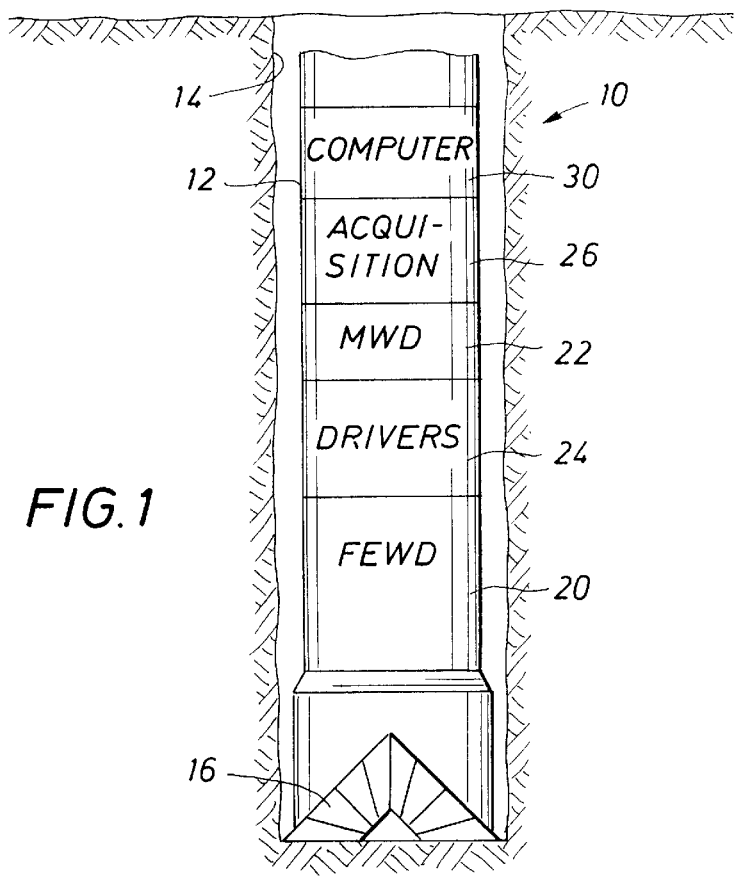
FIG. 1 illustrates a logging-while-drilling bottom hole assembly.

Referring to FIG. 1, there is illustrated a logging-while-drilling apparatus 10 in which embodiments of the invention can be practiced. A drill string 12 is disposed within borehole 14 and includes a drill bit 16 at its lower end. The drill string 12, and the drill bit 16 attached thereto, is rotated by a rotating table (not shown) which engages a kelly (not shown) at the upper end of the drill string 12. Alternatively, the drill string 12 may be rotated from the surface by a "top drive" type of drilling rig. In either case, a device pumps drilling fluid or mud into the drill string downward through a channel in the center of drill string 12. The drilling fluid exits the drill string 12 via ports in the drill bit 16 and then circulates upward in the region between the outside of the drill string 12 and the periphery of the borehole 14. As is well known, the drilling fluid thereby carries formation cuttings to the surface of the earth.

Tools designed for formation evaluation while drilling 20 (LWD), drill string characterization while drilling 22 (MWD), or a combination of both (LWD/MWD) are connected to the drill string 12. A typical MWD tool 22 measures and/or computes the direction, inclination, and rotational orientation of the bottom hole assembly ("tool face"). An MWD tool useful with the subject invention is described, for example, in U.S. Pat. No. 5,473,158. The driving electronics module 24 and acquisition and processor electronics module 26 are coupled to the LWD tool 20. These modules 24, 26 control and obtain measurement information therefrom. The LWD tool 20 contemplated by the subject invention is described below.

Figure 2:
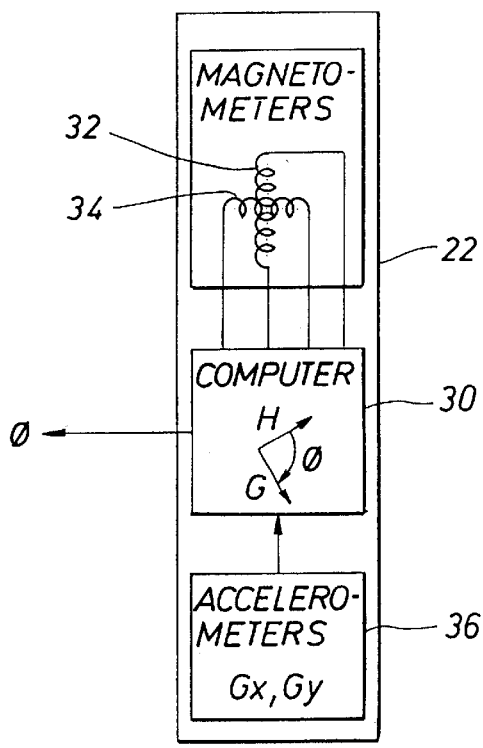
FIG. 2 illustrates a measurement-while-drilling apparatus.

FIG. 2 illustrates the MWD tool 22 which includes magnetometers $H_x$, and $H_y$ (32, 34) oriented along x and y axes of the tool. Such x and y axes are in the plane of a radial cross section of the tool. A z-axis of the tool is oriented along its longitudinal axis. In a similar way, accelerometers $G_x$ and $G_y$ of the accelerometer package 36 (which also includes an accelerometer along the z-axis of the tool) are oriented along the x and y axes of the tool. A microcomputer 30 responds to $H_x$ and $H_y$ signals and $G_x$ and $G_y$ signals to constantly determine an angle φ between an $\vec{H}'$ vector and the $\vec{G}'$ vector, in the cross sectional plane of the MWD tool 22. The $\vec{H}'$ vector represents that portion of a vector pointed to earth's magnetic north pole which is projected onto the x-y plane of MWD tool 22. The $\vec{G}'$ vector represents the down component in the cross sectional plane of tool 22 of the earth's gravity vector. A signal representative of such angle φ is constantly communicated to the downhole computer 30 (which includes a Quadrant/Coil Position Determination program).

Figure 3:
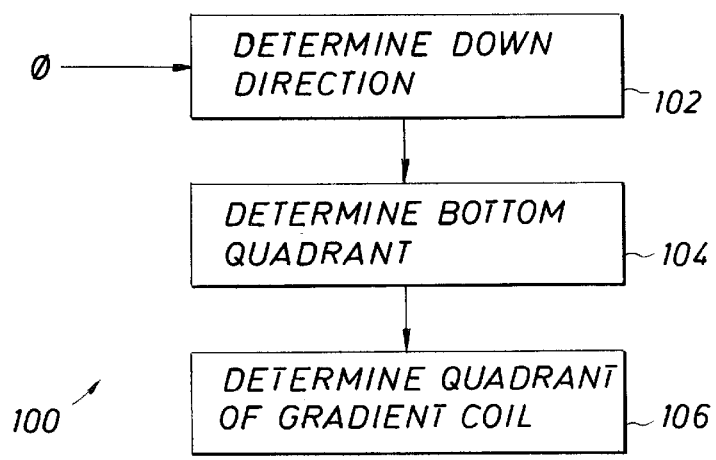
FIG. 3 represents a flow chart of the Quadrant/Coil Position Determination Program.

FIG. 3 is a flow chart which describes the Quadrant/Coil Position Determination Program 100. As explained above, an angle φ is constantly computed between the $\vec{H}'$ vector (a constantly directed vector in the x-y plane for a vector directed to earth's magnetic pole) and a $\vec{G}'$ vector (a constantly directed down vector in the x-y plane of a vector directed to the earth's gravitational center). As the device rotates in the borehole, the x and y axes of the device rotate at the angular speed of the drill string 12 so the x and y components of the $\vec{H}'$ vector and $\vec{G}'$ vector are constantly changing with time. Further, as the device rotates in borehole 14, an angle θ(t) is constantly formed between the tool x-axis and such $\vec{H}'$ vector. The angle θ(t) is determined from the $H_x$ and $H_y$ signals from magnetometers 32 and 34 and the angle varies with time because it is measured from the x-axis of the MWD tool 22 (and the LWD tool 20) to the $\vec{H}'$ vector.

At step 102, the down vector angle, $\angle \vec{D}(t)$, is determined in Quadrant/Coil Position Determination program 100, according to the following relationship, as a function of the x and y axes and time:

$$\theta(t) = \cos^{-1}\left[\frac{H_x(t)}{\sqrt{(H_x(t)^2 + H_y(t)^2)}}\right]. \tag{1}$$

The angle of the down vector is determined in the program as $\angle \vec{D}(t) = \theta(t) - \phi$.

At step 104, four quadrants may be defined by angular ranges about the periphery of the tool:

$Q_{BOT}(t) = \angle \vec{D}(t) - 45°$ to $\angle \vec{D}(t) + 45°$ $Q_{LEFT}(t) = \angle \vec{D}(t) + 45°$ to $\angle \vec{D}(t) + 135°$ $Q_{TOP}(t) = \angle \vec{D}(t) + 135°$ to $\angle \vec{D}(t) + 225°$ $Q_{RIGHT}(t) = \angle \vec{D}(t) + 225°$ to $\angle \vec{D}(t) + 45°$.

The term "quadrant" is used to illustrate the invention where four 90° angular distance segments are defined around the 360° circumference of the MWD device or the LWD tool. Other angular distance segments may be defined, either lesser or greater in number than four, and such segments may be unequal.

Figure 4:
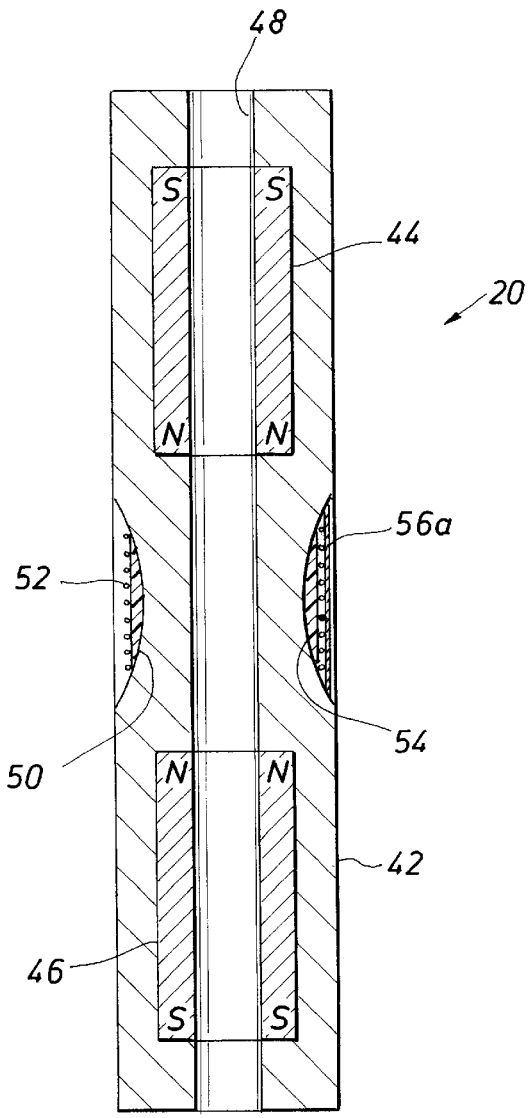
FIG. 4 represents a nuclear magnetic resonance logging-while-drilling tool.

FIG. 4 illustrates a nuclear magnetic resonance (NMR) logging-while-drilling tool 20 in accordance with a preferred embodiment of the invention. The tool 20 is rotationally symmetric about the axis 40 of the drill collar 42, which is substantially aligned with the axis of the borehole. A static magnetic field is produced by tubular, axially polarized, permanent magnets 44, 46 that are mounted inside the drill collar 42. Channel 48 located inside the tool permits drilling mud to flow toward the drill bit. In the region between the magnets 44, 46, there is a recessed area 50. An RF antenna 52 is provided in the recessed area 50. Preferably, the antenna 52 comprises a coil wound circumferentially around the recessed area. The RF field created by such a coil arrangement is substantially axisymmetric. It is within contemplation of the subject invention to utilize the antenna 52 for detecting NMR signals. However, a separate antenna or receiver may be used to detect the signals. A non-conductive material 54 is provided in the recessed area 50 beneath the antenna 52. The material 54 is preferably a ferrite to increase the efficiency of the antenna 52. Alternatively, the material 54 may comprise a plastic, rubber, or a reinforced epoxy composite material.

Still referring to FIG. 4, in order to obtain azimuthal NMR measurements, at least one gradient coil 56 is arranged in the recessed area 50. In a preferred embodiment of the invention, three gradient coils 56a, 56b, and 56c are positioned circumferentially around the recessed area and separated by an angular distance segment of 120°. Other quantities of gradient coils may be defined, either lesser or greater in number than three, and such coils may be separated by angular distances other than 120° and/or unequal angular segments. Each coil 56a, 56b, and 56c is constructed with loops of wire which conform to the curvature of the outer surface of the material 54. The magnetic field produced by each gradient coil 56a, 56b, and 56c in a region of the formation facing the coil is substantially parallel to the static magnetic field produced by the permanent magnets 44, 46. It should be noted that the method and gradient coils of the subject invention can also be used with any tool that generates a rotationally symmetric static magnetic field, for example, the tools disclosed in U.S. Pat. No. 5,757,186 issued to Taicher et al., and U.S. Pat No. 5,280,243 issued to Melvin Miller.

Figure 5:
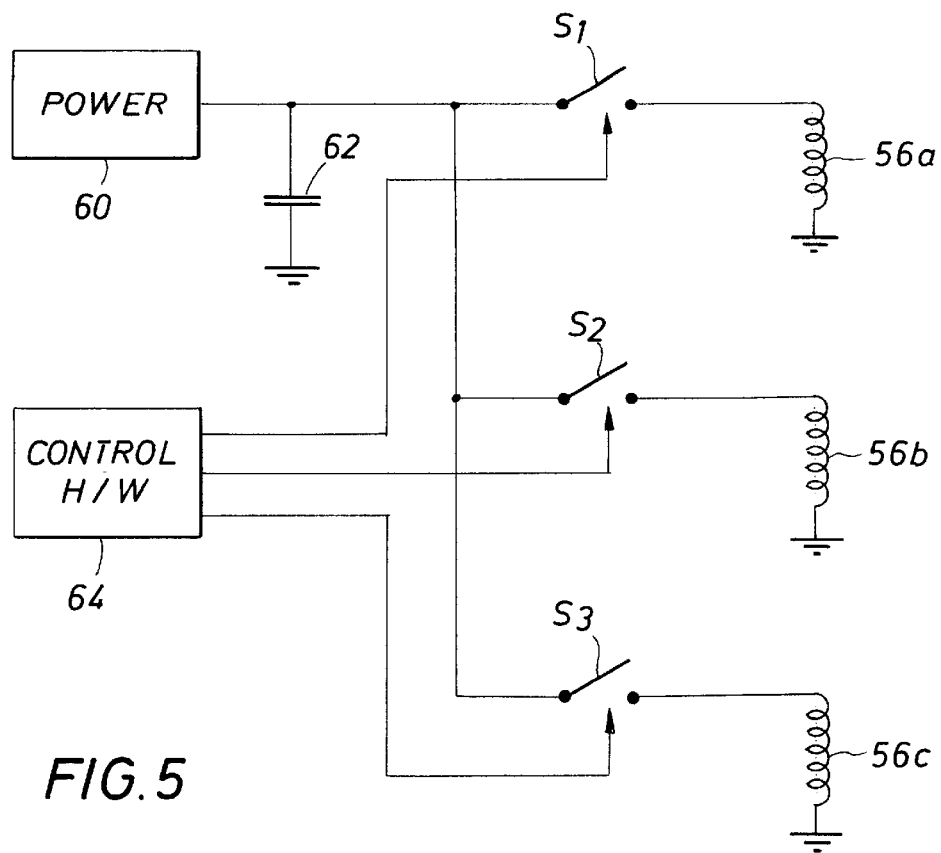
FIG. 5 diagrams the electronic circuitry used in conjunction with the gradient coils of the subject invention.

FIG. 5 is a diagram of the circuitry included in the driving electronics module 24 for use in conjunction with the gradient coils 56a, 56b, and 56c. The driving electronics includes a high voltage power supply 60 and capacitor 62. Switches $S_1$, $S_2$, and $S_3$ are under the control of timing control/coil selection hardware 64. The gradient coils $56_a$, $56_b$, and $56_c$ are coupled, via the switches, to the timing control/coil selection hardware 64.

Figure 6:
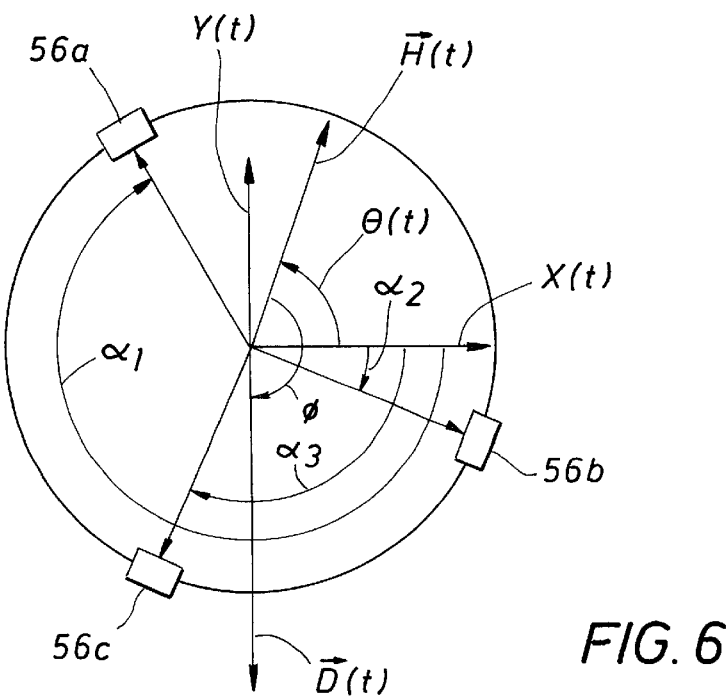
FIG. 6 illustrates the gradient coils in one embodiment of the subject invention.

As FIG. 6 illustrates, the gradient coils 56a, 56b, and 56c are oriented at known angles, $\alpha_1, \alpha_2$, and $\alpha_3$, respectively, from the x-axis. Thus, the angle of each gradient coil is a constant angle, $\alpha$, as measured from the x-axis of the tool 20. Accordingly, the computer program 100 determines which quadrant a coil 56a, 56b, or 56c is in by comparing its angle from the x-axis and $\theta(t)$ with a quadrant defined with respect to the x-axis. The down vector, $\vec{D}$, and four quadrants, $Q_{BOT}$, $Q_{RIGHT}$, $Q_{TOP}$, and $Q_{LEFT}$ are fixed in space, but are defined as a function of time with the turning x and y axes of the LWD device.

As is known to those skilled in the art, in the basic NMR measurement, a pulse sequence is applied to the formation under investigation. In U.S. Pat. No. 5,596,274 issued to Abdurrahman Sezginer and U.S. Pat. No. 5,023,551 issued to Kleinberg et al., a pulse sequence, such as the Carr-Purcell-Meiboom-Gill (CPMG) sequence, first applies an excitation pulse, a 90° pulse, to the formation that rotates the spins into the transverse plane. After the spins are rotated by 90° and start to dephase, the carrier of the refocusing pulses, the 180° pulses, is phase shifted relative to the carrier of the 90° pulse sequence according to the following relationship: $t_{90°_{\pm x}} - t_0 - [t_{180°_y} - t_1 - \text{echo}_{max}{}^{n-t}{}_2]_n$, where the bracketed expression is repeated for n=1,2, . . . N, where N is the number of echoes collected in a single CPMG sequence and the echo spacing is $t_{echo} = 2t_{cp} = t_{180_y} + t_1 + t_2$. $90°_{\pm x}$ denotes an RF pulse that causes the spins to rotate by a 90° angle about the ±x-axis, as commonly defined in the rotating frame of magnetic resonance measurements (phase alternated). The time between application of the 90° pulse and the 180° pulse, $t_0$, is less than $t_{cp}$, half the echo spacing. The CPMG sequence enables acquisition of a symmetric measurement (i.e., a measurement without using the gradient coils). The exact timing parameters, $t_0$, $t_1$, and $t_2$, depend on various factors (e.g., the shape of the applied pulses).

Figure 7A:
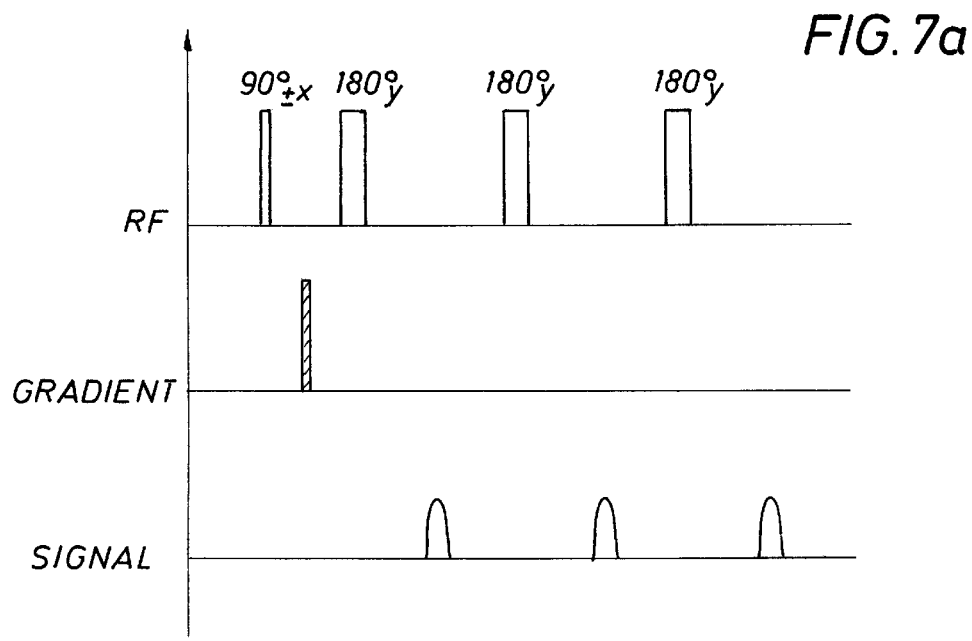
FIG. 7a illustrates the pulse sequence used in a preferred embodiment of the invention.
Figure 7B:
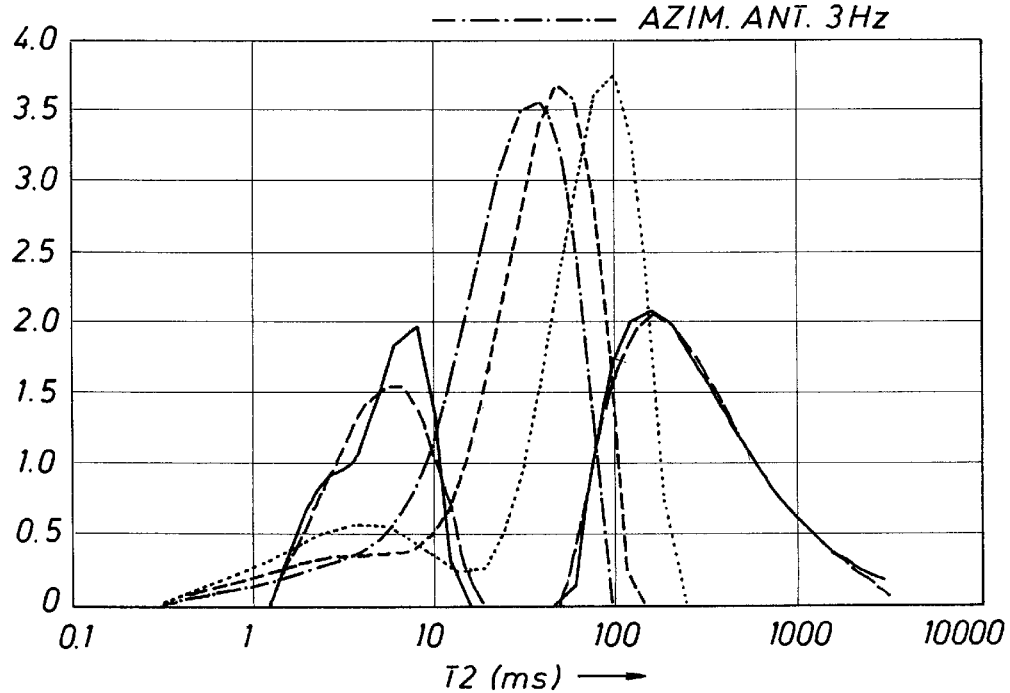
FIG. 7b represents a simulation of the rotation effect on the $T_2$ spectrum using an azimuthal antenna.

In the subject invention, a current pulse applied to gradient coil 56a, 56b, or 56c generates an additional magnetic field, substantially parallel to the static magnetic field. The current pulse is applied between the first 90 and the 180° phase reversing pulse. This is additional field causes an additional phase shift for the spins. Since the 180° phase reversing pulse does not compensate for the additional phase shift, the spins subjected to the additional field do not form a spin-echo. However, for spins not subjected to the additional field, a spin-echo occurs at time $2t_{cp}$ with spin-echoes of successively lower amplitude occurring at time $t_{cp}$ after each phase reversing pulse. The pulse sequence is $t_{90°_{\pm x}} - t_0{}^a - \delta - t_0{}^b - [t_{180°_y} - t_1 - \text{echo}_{max}{}^n - t_2]_n$, where $t_a{}^a$ is the time between the 90° pulse and the gradient pulse of duration $\delta$, $t_0{}^b$ is the time between the gradient pulse and the 180° reversing pulse, and $t_0{}^a + \delta + t_0{}^b = t_0$. In addition, as described before, due to off-resonance effects, out of phase magnetization vanishes within a few echoes. Due to the succeeding $180°_y$ pulses and the inhomogeneous fields, the x-component of the NMR signal will decay within a few echoes. Therefore, we focus only on the y-component of the signal. Thus, neglecting relaxation, the first NMR echo signal can be represented as:

$$\text{Signal} = \Im m[\int_{reR^3}(M_x^0 + iM_y^0)(r)\exp(-i\gamma G(r)\delta)dc(r)],$$

where i is the imaginary complex unit; $\gamma$ is the gyromagnetic ratio; $M_x^0$ and $M_y^0$ are respectively x and y components of the magnetization at location r at the time of the first echo in the absence of the gradient pulse; G(r) is the component of the gradient field parallel to $\vec{B}_0$ at the same location; a is the duration of the gradient pulse; and dc(r) denotes the differential sensitivity of the NMR sonde. FIG. 7b shows a simulation of the rotation effect on the $T_2$ spectrum using an azimuthal antenna. This demonstrates that an accurate $T_2$ spectrum is unobtainable with a rotating azimuthal antenna. However, with the axisymmetric antenna and gradient coil of the subject invention, it is possible to obtain a better $T_2$ spectrum.

The acquisition of phase alternated pulse sequences may be eliminated by using the RingKiller pulse sequence described in U.S. patent application Ser. No. 09/102,719 assigned to Schlumberger Technology Corporation. With that sequence, during a first time period of a single pulse sequence, the NMR measurement includes the desired spin-echoes and the undesired effects, that is, ringing, measurement noise, and baseline shift. During a second time period of the single pulse sequence, the spin-echoes are eliminated but not the undesired effects. Using the signal collected during the second time period, the signals measured during the first time period are corrected to eliminate the ringing component, measurement noise, and baseline shift. It is within contemplation of this invention to use any combination of sequences to eliminate ringing, including, but not limited to, the ringing suppression method described in WO 98/43064 assigned to Numar Corporation.

Depending upon the geometric design of the gradient coils 56a, 56b, and 56c, the duration, and the strength of the current pulse applied to the coil 56a, 56b, or 56c, the spins in a sensitive region (e.g., one quadrant) will dephase in one of the following manners: radial dephasing, azimuthal dephasing, axial dephasing, or incomplete dephasing. Firing a current of sufficient magnitude through the gradient coils causes the additional phase shift of the spins subjected to the magnetic field gradient of the coil to be distributed over a range from −180° to 180° and possibly vary by several multiples of 360° over the sensitive region. For radial, axial, and azimuthal dephasing, a varying additional phase angle is generated so that the response of spins in a sensitive region (e.g., one quadrant) averages to zero.

Figure 8A:
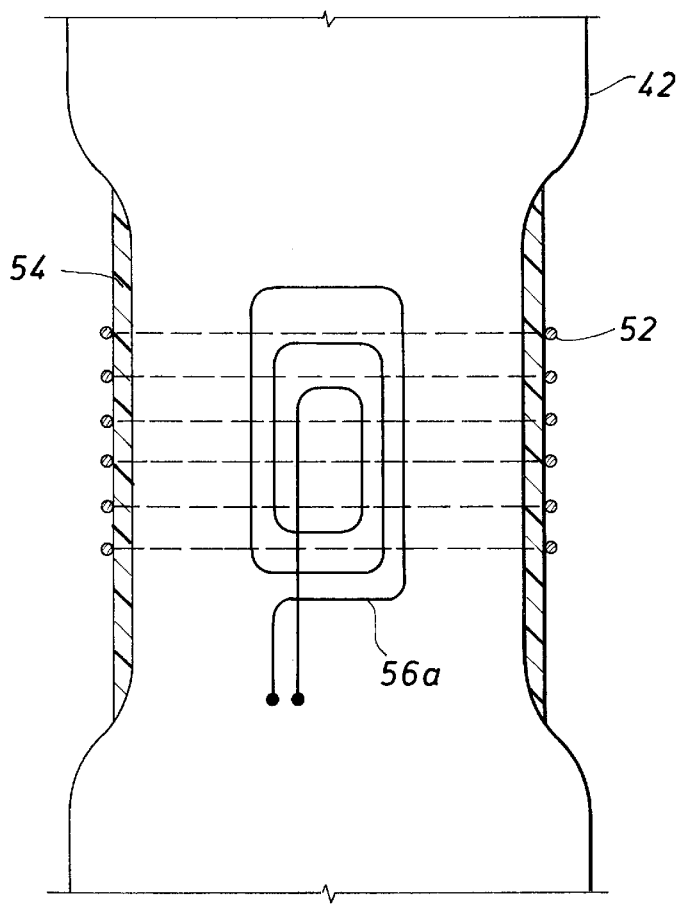
FIGS. 8a–8b illustrate a gradient coil geometry for radial dephasing and the resulting magnetic field strength.
Figure 8B:
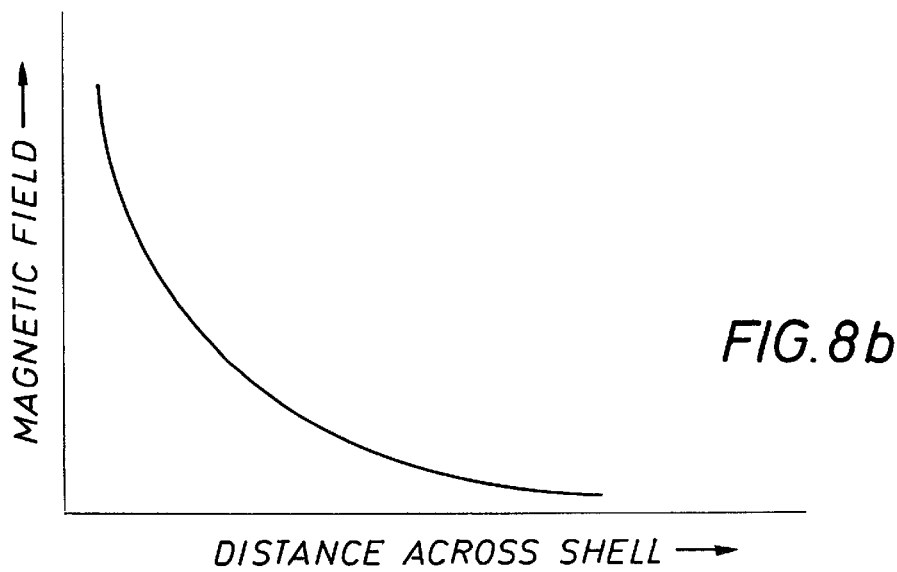

FIG. 8a illustrates a gradient coil geometry useful for radial dephasing. This is achieved by generating a strong gradient field with a single coil so that the additional phase due to the field of the gradient coil 56a, 56b, or 56c varies within the thickness (i.e., shell) of the sensitive region by at least $27\pi$. FIG. 8b depicts the magnetic field strength across the shell. In the portion of the shell close to the gradient coil, spins rotate faster than spins toward an outside portion of the shell.

Figure 9A:
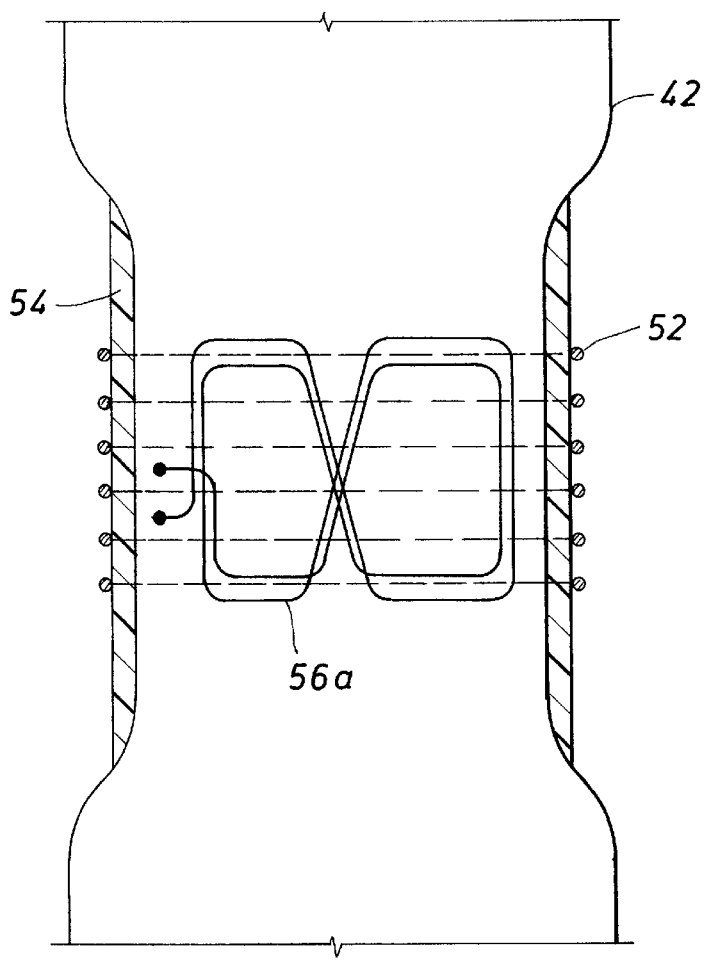
FIGS. 9a–9b illustrate a gradient coil geometry for azimuthal dephasing and the resulting magnetic field strength.
Figure 9B:
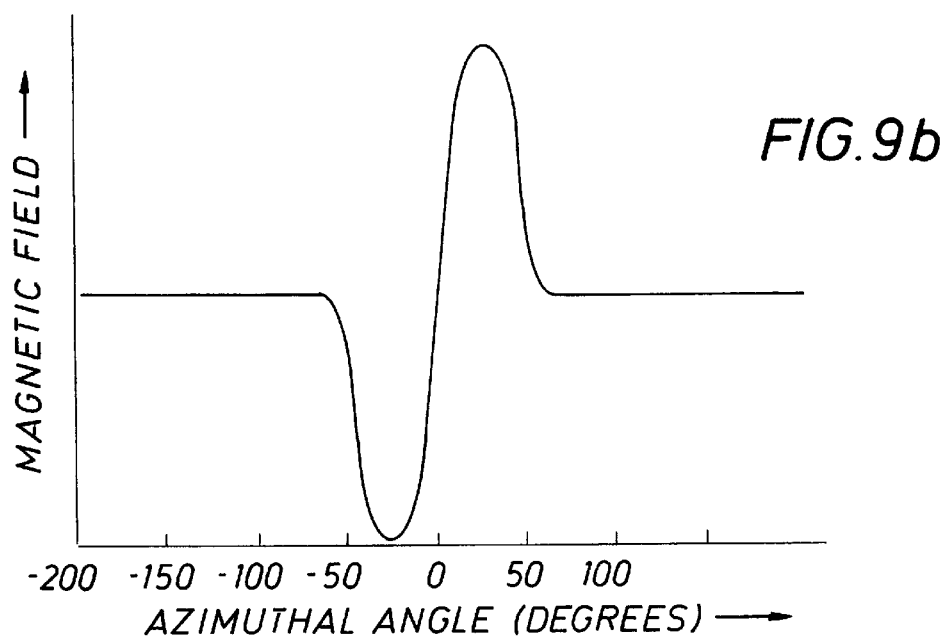

FIG. 9a illustrates a gradient coil geometry useful for azimuthal dephasing. This is achieved by generating a strong gradient field with two coils connected in series such that the current flows in opposite directions in the two coils. When opposite currents are flowing in the two coils, the spins in the vicinity of one coil rotate faster than the average spins and the spins in the vicinity of the other coil rotate more slowly than the average so that the additional phase varies over the azimuth of a part of the sensitive region. FIG. 9b depicts the magnetic field strength along the azimuthal angle $\phi$.

Figure 10A:
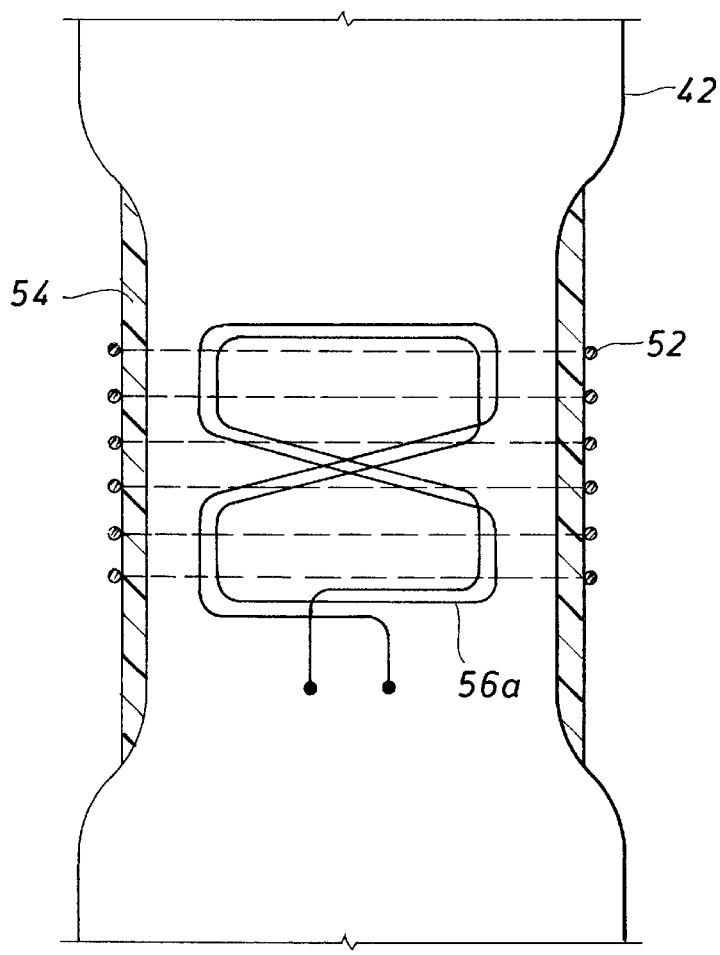
FIGS. 10a–10b illustrate a gradient coil geometry for axial dephasing and the resulting magnetic field strength; and, FIGS. 11a–11b represent the azimuthal distribution of the NMR signal for incomplete and complete dephasing.
Figure 10B:
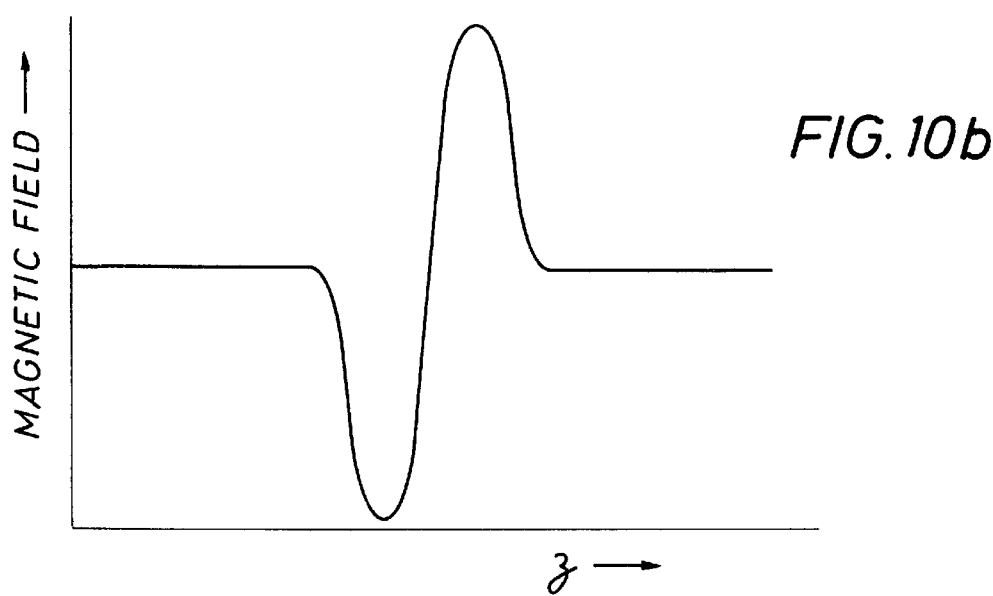

Rotating the azimuthal dephasing coil by 90° results in a gradient coil geometry useful for axial dephasing (See FIG. 10a). The phase angle varies along the longitudinal axis of the tool. FIG. 10b depicts the magnetic field strength along the length of the tool. In all three cases (radial, azimuthal, and axial dephasing), the spatial average of the magnetization over the sensitive region is zero and therefore does not contribute to the measured NMR signal.

In the case of incomplete dephasing, the strength of the current through the gradient coil 56a, 56b, or 56c is weaker than the previously described three cases, and the additional phase shift does not vary strongly enough to cause a complete averaging out to zero of the magnetization over the sensitive region. Nevertheless, the additional gradient field causes a phase shift of the spins in the sensitive region with respect to the phase of the spins in the other regions around the tool (i.e., the spins not subjected to the additional field). In this case, the average of the magnetization over the sensitive region is non-zero and has a different phase than the net magnetization in the remaining portion of the investigation region and the spins still experience a phase shift.

Since the detected NMR signal is phase sensitive (i.e., only contributions with a certain phase are measured), an additional phase shift in the direction of the gradient coil 56a, 56b, or 56c is sufficient to perform an azimuthal measurement. Incomplete dephasing is possible with any of the geometric designs shown in FIGS. 8a, 9a, and 10a.

The gradient coils offer a number of advantages for obtaining azimuthal measurements. First, a coil only has to be properly positioned in a desired quadrant for the duration of the gradient pulse rather than during the entire pulse sequence. Second, because the spin-echoes are detected by the axisymmetric antenna, long echo trains can be recorded while the tool rotates in the borehole. Third, the coil simplifies the design of an NMR-LWD tool because the coil does not have the tuning requirements of an RF antenna. Fourth, the same antenna can be used to make symmetric and axisymmetric measurements. Fifth, the coils can be used to obtain NMR measurements with excellent spatial resolution, particularly vertical resolution.

Different modes for obtaining azimuthal NMR measurements are contemplated by the present invention. For a "simple spoiling" mode, at least one coil is used to spoil the spins in a selected quadrant, however, more coils may be used to spoil a plurality of quadrants. In either case, two measurements are obtained: a symmetric phase alternated pulse sequence (PAPS) with a fixed wait time followed by a gradient PAPS, having a variable wait time, with the selected quadrant spoiled by firing the coil in the quadrant. In a preferred embodiment of the invention, the aforementioned gradient pulse sequence is used. The azimuthal measurement is created by subtracting the gradient measurement from the symmetric measurement. In this mode, one symmetric measurement is obtained for every two PAPS and one azimuthal scan is obtained for every eight PAPS. The measurement noise for the azimuthal measurement is higher than the noise in the symmetric or gradient measurement because the two measurements are combined.

It is possible to reduce the noise contribution by combining different single quadrant spoiling measurements. In this case, four gradient PAPS measurements are obtained by spoiling each quadrant. Then, the measurements are combined to create a synthetic azimuthal and symmetric measurement according to the following relationship: Azimuthal $(PAPSQ_{BOT}) = -\frac{2}{3} PAPS\ Q_{BOT} + \frac{1}{3}\ (PAPSQ_{TOP} + PAPSQ_{RIGHT} + PAPSQ_{LEFT})$ and Symmetric $(PAPS) = \frac{1}{3}$ $(PAPS\ Q_{BOT} + PAPSQ_{TOP} + PAPSQ_{RIGHT} + PAPSQ_{LEFT})$. For this mode, the symmetric PAPS and the gradient PAPS both have a variable wait time.

The gradient coils may be used to generate azimuthal information for a wireline tool and for an LWD tool when the drill string does not rotate (sliding). The simple spoiling mode may be utilized. At least one coil is used to spoil the spins in the quadrant faced by the coil, however, if the tool has more than one coil then spins may be spoiled for each quadrant faced by a coil. If the tool contains a coil for each quadrant, it is possible to create a synthetic azimuthal and symmetric measurement.

Figure 11A:
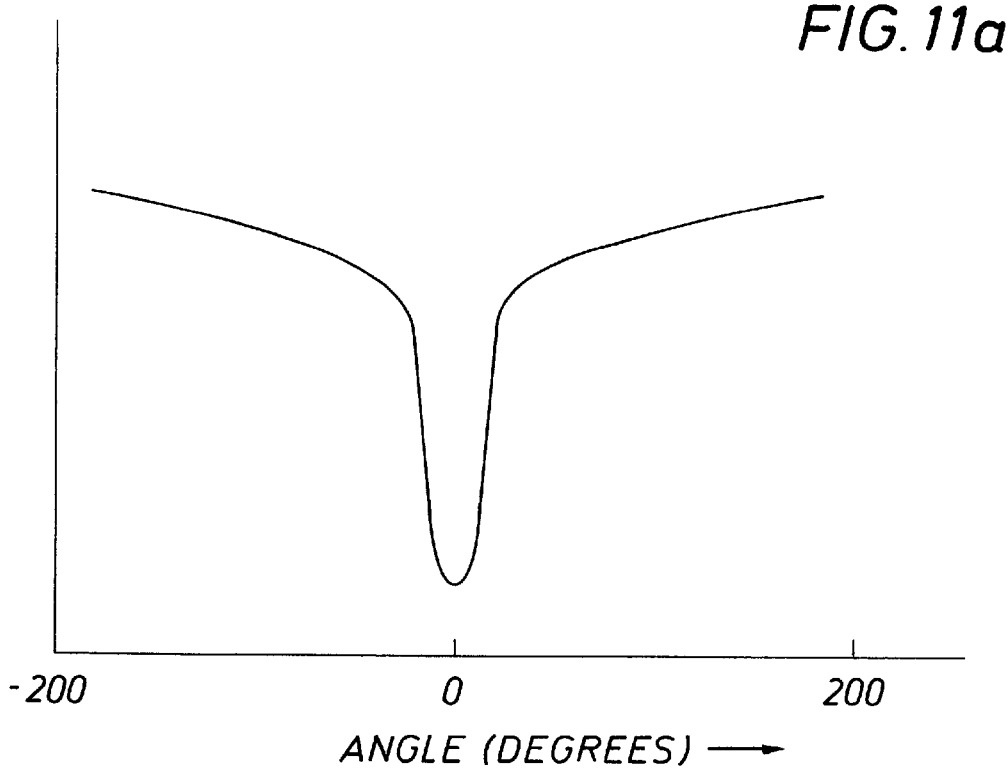
Figure 11B:
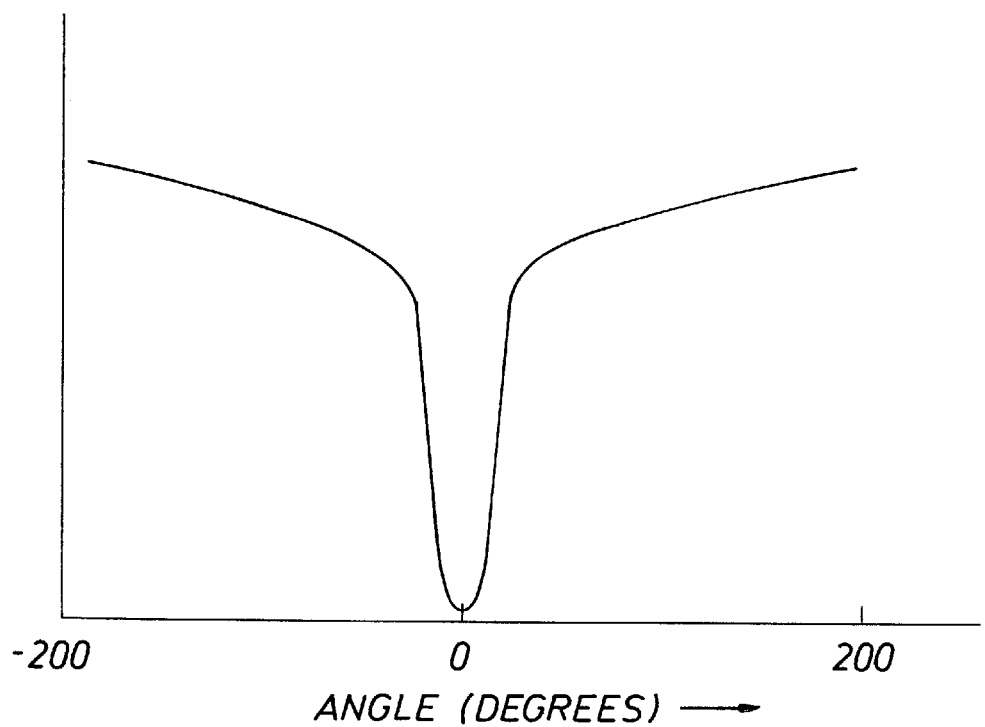

FIGS. 11a and 11b respectively represent the azimuthal distribution of the NMR signal for incomplete and complete dephasing. Each azimuthal distribution is referred to as a "kernel" (denoted by $k(\theta)$). At a particular drilling depth, the azimuthal measurement function $S(\theta)$ acquired by the tool 20 is the convolution of the kernel with the actual azimuthal NMR information function $f(\phi)$ (e.g., porosity, bound fluid volume, $T_2$, or permeability) according to the following relationship:

$$S(\theta) = \int_\theta K(\theta - \varphi) f(\varphi) d\varphi. \quad (2)$$

Therefore, reconstruction of the NMR information, f, in the formation consists of solving a deconvolution problem from the acquired signal S with the kernel K. This problem can be solved in the Fourier space as:

$$\hat{f} = \frac{\hat{S}}{\hat{K}}.$$

The azimuthal function $f(\phi)$ will always be a periodic function of the azimuth. Therefore, it can be expanded into a Fourier series:

$$f(\varphi) = \frac{a_0}{\sqrt{2\pi}} + \frac{1}{\sqrt{\pi}} \sum_{l=1}^{\infty} (a_l \cos(l\varphi) + b_l \sin(l\varphi)), \quad (3)$$

where the Fourier coefficients $a_0$, $a_l$, and $b_l$ can be written as:

$$a_0 = \frac{1}{\sqrt{2\pi}} \int_0^{2\pi} f(\varphi) d\varphi, \quad (4)$$

$$a_l = \frac{1}{\sqrt{\pi}} \int_0^{2\pi} f(\varphi) \cos(l\varphi) d\varphi, \quad (5)$$

$$b_l = \frac{1}{\sqrt{\pi}} \int_0^{2\pi} f(\varphi) \sin(l\varphi) d\varphi. \quad (6)$$

The actual measurement does not give directly the function $f(\phi)$, but rather its convolution with the azimuthal sensitivity kernel $k(\phi)$, which is defined by the gradient coil. The measured signal $v(\phi)$ can be written as:

$$v(\varphi) = \int_0^{2\pi} f(x) k(\phi - x) dx = \frac{a_0}{\sqrt{2\pi}} \int_0^{2\pi} k(x) dx + \frac{1}{\sqrt{\pi}} \sum_{l=1}^{\infty} \left( a_l \int_0^{2\pi} \cos(lx) k(\varphi - x) dx + b_l \int_0^{2\pi} \sin(lx) k(\varphi - x) dx \right). \quad (7)$$

Using:

$$\int_0^{2\pi} \cos(lx) k(\varphi - x) dx = \cos(l\varphi) \int_0^{2\pi} \cos(lx) k(x) dx + \sin(l\varphi) \int_0^{2\pi} \sin(lx) k(x) dx, \quad (8)$$

and $$\int_0^{2\pi} \sin(lx) k(\varphi - x) dx = \sin(l\varphi) \int_0^{2\pi} \cos(lx) k(x) dx - \cos(l\varphi) \int_0^{2\pi} \sin(lx) k(x) dx, \quad (9)$$

the measured signal $v(\phi)$ can be written as Eq. (10):

$$v(\varphi) = \frac{a_0}{\sqrt{2\pi}} \int_0^{2\pi} k(x) dx + \frac{1}{\sqrt{\pi}} \sum_{l=1}^{\infty} \left( (a_l \cos(l\varphi) + b_l \sin(l\varphi)) \int_0^{2\pi} k(x) \cos(lx) dx + (a_l \sin(l\varphi) - b_l \cos(l\varphi)) \int_0^{2\pi} k(x) \sin(lx) dx \right).$$

Using the Fourier expansion of the kernel $k(\phi)$:

$$k(\varphi) = \frac{x_0}{\sqrt{2\pi}} + \frac{1}{\sqrt{\pi}} \sum_{l=1}^{\infty} (x_l \cos(l) + y_l \sin(l)), \quad (11)$$

with:

$$x_0 = \frac{1}{\sqrt{2\pi}} \int_0^{2\pi} k(x) dx, \quad (12)$$

$$x_l = \frac{1}{\sqrt{\pi}} \int_0^{2\pi} k(x) \cos(lx) dx, \text{ and} \quad (13)$$

$$y_l = \frac{1}{\sqrt{\pi}} \int_0^{2\pi} k(x) \sin(lx) dx, \quad (14)$$

the measured signal $v(\phi)$ can be written as:

$$v(\varphi) = a_0 x_0 + \sum_{l=1}^{\infty} ((a_l x_l - b_l y_l) \cos(l\varphi) + (a_l y_l + b_l x_l) \sin(l\varphi)), \quad (15)$$

which is the Fourier expansion of the measurement signal $v(\phi)$. Since the kernel $k(\phi)$ is symmetric, the Fourier coefficients $y_1$ vanish. Eq. 15 becomes:

$$v(\varphi) = a_0 x_0 + \sum_{l=1}^{\infty} (a_l x_l \cos(l\varphi) + b_l x_l \sin(l\varphi)). \quad (16)$$

To reconstruct the function $f(\phi)$ out of the measurements, it is necessary to determine the Fourier coefficients $a_0$, $a_1$, and $b_1$. These coefficients can be determine by inverting the linear system of Eq. 16. To invert Eq. 16, the Fourier expansion is restricted to a predetermined order. This restriction is equivalent to a deconvolution using the projection of the kernel function onto the first few basis functions of the Fourier expansion, i.e., the reconstruction of the kernel using only the first few Fourier coefficients.

For the measured NMR data described in Eq. 16, the higher order Fourier coefficients of the formation function $f(\phi)$ do not influence the measurements very strongly, if the corresponding Fourier coefficients of the kernel are small. Therefore, it is impossible to determine these higher order coefficients from the measured data, particularly if the measurements are noisy. On the other hand, a restriction of Eq. 16 to too few coefficients can lead to a incorrect determination of the lower order coefficients, if the influence of the higher order coefficients is not negligible. In these cases, the higher order Fourier coefficients of $f(\phi)$ would influence the estimations of the lower order coefficients. The order to which Eq. 16 can be solved depends on the number of measured data, the quality of the data, and the Fourier coefficients of the kernel.

Restricting Eq. 16 to the order K, introducing the 2K+1 dimensional vector $\vec{a} = (a_0, a_1, b_1, \ldots, a_K, b_K)$, and defining $\vec{v}$ as the N dimensional vector of measurements taken in the directions $\phi_i, \forall i=1, \ldots, N$, the vector $\vec{i}$ can be written as:

$$\vec{v} = X\vec{a},\qquad(17)$$

where the matrix X is defined as:

$$X = \begin{pmatrix} x_0 & x_1\cos(\varphi_1) & x_1\sin(\varphi_1) & \cdots & x_K\cos(K\varphi_1) & x_K\sin(K\varphi_1) \\ x_0 & x_1\cos(\varphi_2) & x_1\sin(\varphi_2) & \cdots & x_{KI}\cos(K\varphi_2) & x_K\sin(K\varphi_2) \\ \vdots & \vdots & \vdots & \ddots & \vdots & \vdots \\ x_0 & x_1\cos(\varphi_{NI}) & x_1\sin(\varphi_N) & \cdots & x_K\cos(K\varphi_N) & x_K\sin(K\varphi_N) \end{pmatrix}.\qquad(18)$$

The least squares solution of Eq. (17) is:

$$\vec{a} = (X'X)^{-1}X'\vec{v}.\qquad(19)$$

A regularization term can be included in Eq. (19) to reduce the statistical uncertainty of the estimated Fourier coefficients. The standard deviation $\vec{\sigma}_a$ of the Fourier coefficients can be computed using the standard deviation $\sigma$ of each azimuthal measurement:

$$(\vec{\sigma}_a)_i = \sigma \|((X'X)^{-1}X')_i\|,\qquad(20)$$

where $((X'X)^{-1}X')_i$ is the $i^{-th}$ row vector of the matrix $(X'X)^{-1}X'$.

Defining the vector $$\vec{r}(\varphi) = \qquad(21)$$

$$\left(\frac{1}{\sqrt{2\pi}}, \frac{1}{\sqrt{\pi}}\cos(\varphi), \frac{1}{\sqrt{\pi}}\sin(\varphi), \ldots, \frac{1}{\sqrt{\pi}}\cos(K\varphi), \frac{1}{\sqrt{\pi}}\sin(K\varphi)\right)',$$

the reconstruction $f_R(\phi)$ of the formation function $f(\phi)$ in any direction $\phi$ is:

$$f_R(\phi) = \vec{r}(\phi)'\vec{a}.\qquad(22)$$

The standard deviation $\sigma_f(\phi)$ depends on the azimuth and can be written as:

$$\sigma_f(\varphi) = \sqrt{\sum_{i=1}^{2K+1} r_i^2(\varphi)(\vec{\sigma}_a)_i^2}.\qquad(23)$$

The acquisition of azimuthal data depends on the tool rotation. In the subject invention, the most efficient way to obtain azimuthal information for a complete scan of the borehole is to sample so that the measurements are equally distributed over the scan. If the data acquisition is made at fixed time intervals, it is not always guaranteed that all directions ($Q_{BOT}$, $Q_{RIGHT}$, $Q_{TOP}$, and $Q_{LEFT}$) can be covered within one scan. One solution to achieve a full coverage is to choose for each measurement the best direction based on the already acquired data for the current scan. In order to have different directions to choose from, the LWD tool 20 is equipped with gradient coils mounted at 120° separation. At each acquisition opportunity, it is possible to choose the gradient coil that is most beneficial for the actual scan based on the already acquired data. Since the Fourier coefficients are computed out of the performed measurements by an inversion, a criterion for choosing new directions is to minimize the condition number of the matrix X. Another criterion is to choose the new direction in a way such that the measured directions are distributed equally around the borehole. In this case, each new direction is chosen to maximize its distance (difference in the azimuths) towards its closest neighbor.

A second possibility for acquiring azimuthal data is the binning of the measured data. In this acquisition scheme, a plurality of azimuthal bins are defined and each NMR measurement is added to the content of the buffer associated with the bin in which the measurement was taken. For the LWD tool 20, seven bins are preferable. To obtain a good statistic for each bin and to ensure that in each bin there are enough measurements, this scheme requires numerous individual measurements, e.g., ten measurements per bin or 70 measurements per scan.

A third possibility for acquiring azimuthal data is to perform one measurement for each quadrant, $Q_{BOT}$, $Q_{RIGHT}$, $Q_{TOP}$, and $Q_{LEFT}$, for an entire scan. To ensure these measurements are always obtained in the desired quadrant, windows in time are defined during which it is possible to acquire data. The actual time of the data acquisition within each window is controlled by the drill string rotation. A preferred method for acquiring data by directionally based firing of a gradient coil is to approximate the kernel by a rectangular functional. In this case, a measurement a, taken in a particular direction, for example $Q_{BOT}$, can be written as:

$$a_1 = x_2 + x_3 + x_4,\qquad(24)$$

where $x_2$, $x_3$, and $x_4$ are the values of the measured function in the other three directions (i.e., the directions in which the gradient coil does not point.) Combining the measurements in all four directions results in the following system of equations:

$$\vec{a} = M\vec{x},\qquad(25)$$

with the matrix:

$$M = \begin{pmatrix} 0 & 1 & 1 & 1 \\ 1 & 0 & 1 & 1 \\ 1 & 1 & 0 & 1 \\ 1 & 1 & 1 & 0 \end{pmatrix}.\qquad(26)$$

The solution of Eq. 26 is $\vec{x} = M^{-1}\vec{a}$ with the matrix:

$$M^{-1} = \frac{1}{3}\begin{pmatrix} -2 & 1 & 1 & 1 \\ 1 & -2 & 1 & 1 \\ 1 & 1 & -2 & 1 \\ 1 & 1 & 1 & -2 \end{pmatrix}.\qquad(27)$$

The foregoing description of the preferred and alternate embodiments of the present invention have been presented for purposes of illustration and description. It is not intended to be exhaustive or limit the invention to the precise form disclosed. With the acquisition of azimuthal data, the subject invention may perform e.g., porosity, bound fluid volume (BFV), $T_2$, $T_1$, and permeability measurements. It is also possible to perform azimuthal magnetic resonance imaging, which is useful for interpreting heterogenous formations and performing geologically based steering in deviated or horizontal boreholes. Obviously, many modifications and variations will be apparent to those skilled in the art. For example, the functionality of the MWD tool 22 may also be performed in the LWD tool 20 or divided between the MWD 22 and LWD 20 tools. Also, with a wireline tool, the gradient coil(s) may be located on a pad connected to the tool. Those skilled in the art will appreciate that the method and gradient coil(s) of the subject invention are useful for eliminating the magnetic resonance signal of the borehole fluids, obtaining axially resolved NMR measurements, or NMR measurements with improved vertical resolution. For example, the length of the recessed area 50 along the longitudinal axis of the borehole can define the axial extent of an investigation region. A gradient coil or a plurality of gradient coils can be oriented, at known positions along the longitudinal axis of the borehole, within the recessed area 50. A current pulse applied to the gradient coil(s) will dephase the spins in an axial segment of the formation. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

We claim:

1. An apparatus for determining a nuclear magnetic resonance property in an investigation region of earth formations surrounding a borehole, comprising:
   a) a logging device moveable through the borehole;
   b) means in the logging device for applying a static magnetic field circumferentially around the borehole and into the investigation region as the logging device rotates in the borehole;
   c) antenna means in the logging device for applying an RF magnetic field circumferentially around the borehole and into the investigation region as the logging device rotates in the borehole whereby the antenna means induces a plurality of spin-echo signals from selected nuclei of the formation;
   d) gradient means in the logging device for applying a magnetic field gradient to dephase spins in a portion of the investigation region; and
   e) means for detecting nuclear magnetic resonance signals from the investigation region.

2. The apparatus of claim 1 further comprising means for partitioning a cross-section of the formation into a plurality of angular distance segments around the borehole wherein the gradient means alters the phase of spins by spatially varying the static magnetic field strength in at least one segment so that a net magnetization over the segment is substantially zero.

3. The apparatus of claim 2 wherein the phase of spins changes radially over the segment.

4. The apparatus of claim 2 wherein the phase of spins changes azimuthally over the segment.

5. The apparatus of claim 2 wherein the phase of spins changes axially over the segment.

6. The apparatus of claim 1 further comprising means for partitioning a cross-section of the formation into a plurality of angular distance segments around the borehole and means for altering the phase of spins in at least one segment by applying the gradient field substantially parallel to the static magnetic field so that a net magnetization over the segment is non-zero and has a different phase than the net magnetization in the remaining portion of the investigation region.

7. The apparatus of claim 6 wherein the phase of spins changes radially over the segment.

8. The apparatus of claim 6 wherein the phase of spins changes azimuthally over the segment.

9. The apparatus of claim 6 wherein the phase of spins changes axially over the segment.

10. The apparatus of claim 7 wherein the gradient means comprises a single coil.

11. The apparatus of claim 8 wherein the gradient means comprises at least two coils, the at least two coils are connected so that the current flows in opposite directions.

12. The apparatus of claim 9 wherein the gradient means comprises at least two coils, the at least two coils are connected so that the current flows in opposite directions.

13. The apparatus of claim 8 wherein the gradient means comprises a coil.

14. The apparatus of claim 13 wherein the coil has at least two nonconcentric loops.

15. The apparatus of claim 14 wherein the current flows in opposite directions in the nonconcentric loops.

16. A method for measuring a nuclear magnetic resonance property in an investigation region of earth formations surrounding a borehole, comprising the steps of:
   a) drilling a borehole in the formation with a logging-while-drilling device;
   b) measuring the nuclear magnetic resonance property while drilling the borehole, comprising the steps of:
      i) applying a static magnetic field circumferentially around the borehole and into the investigation region as the logging device rotates in the borehole;
      ii) applying an RF magnetic field circumferentially around the borehole and into the investigation region as the logging device rotates in the borehole;
      iii) inducing a plurality of spin-echo signals from selected nuclei of the formation;
      iv) applying a magnetic field gradient to dephase spins in a portion of the investigation region; and
      v) detecting nuclear magnetic resonance signals from the investigation region.

17. The method of claim 16 further comprising the steps of partitioning a cross-section of the formation into a plurality of angular distance segments around the borehole and altering the phase of spins in at least one segment by spatially varying the static magnetic field strength so that a net magnetization within the segment is zero.

18. The method of claim 17 further comprising the step of radially changing the phase of spins within the segment.

19. The method of claim 17 further comprising the step of azimuthally changing the phase of spins within the segment.

20. The method of claim 17 further comprising the step of axially changing the phase of spins within the segment.

21. The method of claim 17 further comprising the step of generating a sequence of pulses and spin-echoes which provide an azimuthally resolved nuclear magnetic resonance measurement.

22. The method of claim 21 further comprising the step of generating a first pulse sequence comprising a plurality of phase alternated RF pulses and spin-echoes and generating a second pulse sequence comprising a plurality of phase alternated RF pulses, at least one gradient pulse, and spin-echoes.

23. The method of claim 22 wherein the second pulse sequence is:

$$t_{90°\pm x} - t_0^a - \delta - t_0^b - \left[t_{180°y} - t_1 - echo_{max}^n - t_2\right]_n,$$

where $t_0^a$ is the time between a 90° pulse and a gradient pulse of duration $\delta$, $t_0^b$ is the time between the gradient pulse and a 180° reversing pulse, and $t_0^a + \delta + t_0^a = t_0$.

24. The method of claim 22 further comprising the steps of applying the second pulse sequence to at least one segment and applying the first pulse sequence to the remaining plurality of angular distance segments.

25. The method of claim 24 wherein the plurality of angular segments comprises at least four segments.

26. The method of claim 22 wherein the first pulse sequence is applied to at least one segment.

27. The method of claim 21 further comprising the step of generating a pulse sequence comprising a plurality of phase alternated RF pulses, at least one gradient pulse, and spin-echoes.

28. The method of claim 27 further comprising the step of applying the pulse sequence to at least one segment.

29. The method of claim 16 wherein the magnetic gradient field has a polarization orientation in the investigation region substantially the same as the static magnetic field.

30. The method of claim 16 further comprising the steps of partitioning a cross-section of the formation into a plurality of angular distance segments around the borehole and altering the phase of spins in at least one segment by applying the gradient field substantially parallel to the static magnetic field so that a net magnetization over the segment is non-zero and has a different phase than the net magnetization in the remaining portion of the investigation region.

31. The method of claim 30 further comprising the step of radially changing the phase of spins over the segment.

32. The method of claim 30 further comprising the step of azimuthally changing the phase of spins over the segment.

33. The method of claim 30 further comprising the step of axially changing the phase of spins over the segment.

34. The method of claim 30 further comprising the step of generating a sequence of pulses and spin-echoes which provide an azimuthally resolved nuclear magnetic resonance measurement.

35. The method of claim 34 further comprising the step of generating a first pulse sequence comprising a plurality of phase alternated RF pulses and spin-echoes and generating a second pulse sequence comprising a plurality of phase alternated RF pulses, at least one gradient pulse, and spin-echoes.

36. The method of claim 35 wherein the second pulse sequence is:

$$t_{90°_{\pm x}} - t_0^a - \delta - t_0^b - \left[t_{180°_y} - t_1 - echo_{max}^n - t_2\right]_n,$$

where $t_0^a$ is the time between a 90° pulse and a gradient pulse of duration $\delta$, $t_0^b$ is the time between the gradient pulse and a 180° reversing pulse, and $t_0^a + \delta + t_0^b = t_0$.

37. The method of claim 35 further comprising the step of applying the second pulse sequence to the at least one segment and applying the first pulse sequence to the remaining plurality of angular distance segments.

38. The method of claim 37 wherein the plurality of angular segments comprises at least four segments.

39. The method of claim 35 wherein the first pulse sequence is applied to at least one segment.

40. The method of claim 34 further comprising the step of generating a pulse sequence comprising a plurality of phase alternated RF pulses, at least one gradient pulse, and spin-echoes.

41. The method of claim 40 further comprising the step of applying the pulse sequence to at least one segment.

42. The method of claim 30 wherein the gradient field has an orientation in the investigation region substantially the same as that of the static magnetic field.

43. The method of claim 21 wherein during a single pulse sequence, the step of generating a sequence of pulses and spin-echoes comprises the steps of:

i) during a first time period, applying a first plurality of RF pulses and at least one gradient pulse in the investigation region and measuring the generated signals in the investigation region, the measured signals comprise a ringing component and spin-echoes;

ii) canceling the spin-echoes;

iii) during a second time period, applying a second plurality of RF pulses and at least one gradient pulse in the investigation region and measuring the generated signals in the investigation region, the measured signals comprise the ringing component and substantially exclude the spin-echoes; and, iv) correcting the signals measured during the first time period to eliminate the ringing component.

44. The method of claim 34 wherein during a single pulse sequence, the step of generating a sequence of pulses and spin-echoes comprises the steps of:

i) during a first time period, applying a first plurality of RF pulses and at least one gradient pulse in the investigation region and measuring the generated signals in the investigation region, the measured signals comprise a ringing component and spin-echoes;

ii) canceling the spin-echoes;

iii) during a second time period, applying a second plurality of RF pulses and at least one gradient pulse in the investigation region and measuring the generated signals in the investigation region, the measured signals comprise the ringing component and substantially exclude the spin-echoes; and, iv) correcting the signals measured during the first time period to eliminate the ringing component.

45. The method of claim 16 further comprising the step of positioning a gradient means opposite the at least one segment while applying the magnetic field gradient.

46. The method of claim 22 wherein the step of generating a first pulse sequence further comprises the step of applying a fixed wait time.

47. The method of claim 22 wherein the step of generating a first pulse sequence further comprises the step of applying a variable wait time.

48. The method of claim 22 wherein the step of generating a second pulse sequence further comprises the step of applying a variable wait time.

49. The method of claim 27 wherein the step of generating a pulse sequence further comprises the step of applying a fixed wait time.

50. The method of claim 45 further comprising the step of defining an azimuthal sensitivity kernel, $k(\phi)$ using the current flowing through the gradient means.

51. The method of claim 45 further comprising the step of measuring the detected nuclear magnetic resonance signals wherein the measured signals, $v(\phi)$, comprise a convolution of an azimuthal function, $f(\phi)$, with the azimuthal sensitivity kernel, $k(\phi)$.

52. The method of claim 51 further comprising the step of reconstructing the azimuthal function, $f(\phi)$, from the measured signals.

53. The method of claim 52 wherein the reconstructing step further comprises the steps of: determining a first Fourier expansion of the azimuthal sensitivity kernel, $k(\phi)$; determining a second Fourier expansion of the measured signals, $v(\phi)$; and determining a plurality of Fourier coefficients of the azimuthal function, $f(\phi)$.

54. The method of claim 16 further comprising the step of measuring the detected nuclear magnetic resonance signals at fixed time intervals.

55. The method of claim 16 further comprising the step of measuring the detected nuclear magnetic resonance signals at selected positions over an azimuthal scan of the borehole.

56. The method of claim 30 further comprising the step of obtaining at least one measurement of the detected nuclear magnetic resonance signals from each of the plurality of angular distance segments.

57. The method of claim 16 further comprising the steps of defining at least one time window and measuring the detected nuclear magnetic resonance signals within the time window.

58. The method of claim 16 further comprising the steps of measuring the detected nuclear magnetic resonance signals, and partitioning the measured signals into a plurality of bins.

59. The method of claim 58 further comprising the step of partitioning a cross-section of the formation into a plurality of angular distance segments wherein each bin represents the measured signals from at least one of the angular distance segments.

60. A method for nuclear magnetic resonance imaging of an investigation region of earth formations surrounding a borehole, comprising the steps of:
 a) applying a static magnetic field circumferentially around the borehole and into the investigation region as the logging device rotates in the borehole;
 b) applying an RF magnetic field circumferentially around the borehole and into the investigation region as the logging device rotates in the borehole;
 c) inducing a plurality of spin-echo signals from selected nuclei of the formation;
 d) applying a magnetic field gradient to dephase spins in a portion of the investigation region;
 e) detecting nuclear magnetic resonance signals from the investigation region; and,
 f) mapping the signals to an angular or axial position to produce an image of the formation.

61. The method of claim 60 further comprising the steps of partitioning a cross-section of the formation into a plurality of angular distance segments around the borehole and altering the phase of spins in at least one segment by spatially varying the static magnetic field strength so that a net magnetization over the segment is substantially zero.

62. The method of claim 61 further comprising the step of generating a sequence of pulses and spin-echoes which provide an azimuthally resolved image of the formation.

63. The method of claim 60 further comprising the steps of partitioning a cross-section of the formation into a plurality of angular distance segments around the borehole and altering the phase of spins in at least one segment by applying the gradient field substantially parallel to the static magnetic field so that a net magnetization over the segment is non-zero and has a different phase than the net magnetization in the remaining portion of the investigation region.

64. The method of claim 63 further comprising the step of generating a sequence of pulses and spin-echoes which provide an azimuthally resolved image of the formation.

65. The method of claim 62 wherein during a single pulse sequence, the step of generating a sequence of pulses and spin-echoes comprises the steps of:
 i) during a first time period, applying a first plurality of RF pulses and at least one gradient pulse in the investigation region and measuring the generated signals in the investigation region, the measured signals comprise a ringing component and spin-echoes;
 ii) canceling the spin-echoes;
 iii) during a second time period, applying a second plurality of RF pulses and at least one gradient pulse in the investigation region and measuring the generated signals in the investigation region, the measured signals comprise the ringing component and substantially exclude the spin-echoes; and,
 iv) correcting the signals measured during the first time period to eliminate the ringing component.

66. The method of claim 64 wherein during a single pulse sequence, the step of generating a sequence of pulses and spin-echoes comprises the steps of:
 i) during a first time period, applying a first plurality of RF pulses and at least one gradient pulse in the investigation region and measuring the generated signals in the investigation region, the measured signals comprise a ringing component and spin-echoes;
 ii) canceling the spin-echoes;
 iii) during a second time period, applying a second plurality of RF pulses and at least one gradient pulse in the investigation region and measuring the generated signals in the investigation region, the measured signals comprise the ringing component and substantially exclude the spin-echoes; and,
 iv) correcting the signals measured during the first time period to eliminate the ringing component.

67. The method of claim 62 further comprising the steps of generating a first pulse sequence comprising a plurality of phase alternated RF pulses and spin-echoes and generating a second pulse sequence comprising a plurality of phase alternated RF pulses, at least one gradient pulse, and spin-echoes.

68. The method of claim 62 further comprising the step of generating a pulse sequence comprising a plurality of phase alternated RF pulses, at least one gradient pulse, and spin-echoes.

69. The method of claim 64 further comprising the steps of generating a first pulse sequence comprising a plurality of phase alternated RF pulses and spin-echoes and generating a second pulse sequence comprising a plurality of phase alternated RF pulses, at least one gradient pulse, and spin-echoes.

70. The method of claim 64 further comprising the step of generating a pulse sequence comprising a plurality of phase alternated RF pulses, at least one gradient pulse, and spin-echoes.

71. The method of claim 60 further comprising the step of processing the detected signals to optimize the formation image.

72. An apparatus for determining a nuclear magnetic resonance property in an investigation region of earth formations surrounding a borehole, comprising:
 a) a logging device moveable through the borehole;
 b) means in the logging device for applying a static magnetic field circumferentially around the borehole and into the investigation region as the logging device rotates in the borehole;
 c) antenna means in the logging device for applying an RF magnetic field circumferentially around the borehole and into the investigation region as the logging device rotates in the borehole whereby the antenna means induces a plurality of spin-echo signals from selected nuclei of the formation;
 d) a plurality of gradient means positioned around the circumference of the logging device;

e) means for selecting at least one of the gradient means to apply a magnetic field gradient which dephases spins in a portion of the investigation region; and f) means for detecting nuclear magnetic resonance signals from the investigation region.

73. The apparatus of claim 72 further comprising means for partitioning a cross-section of the formation into a plurality of angular distance segments around the borehole wherein the gradient means alters the phase of spins by spatially varying the static magnetic field strength in at least one segment so that a net magnetization over the segment is substantially zero.

74. The apparatus of claim 73 wherein the phase of spins changes radially over the segment.

75. The apparatus of claim 73 wherein the phase of spins changes azimuthally over the segment.

76. The apparatus of claim 73 wherein the phase of spins changes axially over the segment.

77. The apparatus of claim 72 further comprising means for partitioning a cross-section of the formation into a plurality of angular distance segments around the borehole and means for altering the phase of spins in at least one segment by applying the gradient field substantially parallel to the static magnetic field so that a net magnetization over the segment is non-zero and has a different phase than the net magnetization in the remaining portion of the investigation region.

78. The apparatus of claim 77 wherein the phase of spins changes radially over the segment.

79. The apparatus of claim 77 wherein the phase of spins changes azimuthally over the segment.

80. The apparatus of claim 77 wherein the phase of spins changes axially over the segment.

81. The apparatus of claim 73 further comprising means for generating a sequence of pulses and spin-echoes which provide an azimuthally resolved nuclear magnetic resonance measurement.

82. The apparatus of claim 81 further comprising means for generating a first pulse sequence comprising a plurality of phase alternated RF pulses and spin-echoes and means for generating a second pulse sequence comprising a plurality of phase alternated RF pulses, at least one gradient pulse, and spin-echoes.

83. The apparatus of claim 81 further comprising means for generating a pulse sequence comprising a plurality of phase alternated RF pulses, at least one gradient pulse, and spin-echoes.

84. The apparatus of claim 77 further comprising means for generating a sequence of pulses and spin-echoes which provide an azimuthally resolved nuclear magnetic resonance measurement.

85. The apparatus of claim 84 further comprising means for generating a first pulse sequence comprising a plurality of phase alternated RF pulses and spin-echoes and means for generating a second pulse sequence comprising a plurality of phase alternated RF pulses, at least one gradient pulse, and spin-echoes.

86. The apparatus of claim 84 further comprising means for generating a pulse sequence comprising a plurality of phase alternated RF pulses, at least one gradient pulse, and spin-echoes.

87. The apparatus of claim 72 wherein the magnetic gradient field has an orientation in the investigation region substantially the same as the static magnetic field.

88. An apparatus for determining a nuclear magnetic resonance property in an investigation region of earth formations surrounding a borehole, comprising:

a) a logging device moveable through the borehole;

b) means in the logging device for applying a static magnetic field circumferentially around the borehole and into the investigation region;

c) antenna means in the logging device for applying an RF magnetic field circumferentially around the borehole and into the investigation region whereby the antenna means induces a plurality of spin-echo signals from selected nuclei of the formation;

d) a plurality of gradient means positioned around the circumference of the logging device;

e) means for selecting at least one of the gradient means to apply a magnetic field gradient which dephases spins in a portion of the investigation region facing the selected gradient means; and f) means for detecting nuclear magnetic resonance signals from the investigation region.

89. The apparatus of claim 88 further comprising means for partitioning a cross-section of the formation into a plurality of angular distance segments around the borehole wherein the gradient means alters the phase of spins by spatially varying the static magnetic field strength in at least one segment so that a net magnetization over the segment is substantially zero.

90. The apparatus of claim 89 wherein the phase of spins changes radially over the segment.

91. The apparatus of claim 89 wherein the phase of spins changes azimuthally over the segment.

92. The apparatus of claim 89 wherein the phase of spins changes axially over the segment.

93. The apparatus of claim 88 further comprising means for partitioning a cross-section of the formation into a plurality of angular distance segments around the borehole and means for altering the phase of spins in at least one segment by applying the gradient field substantially parallel to the static magnetic field so that a net magnetization over the segment is non-zero and has a different phase than the net magnetization in the remaining portion of the investigation region.

94. The apparatus of claim 93 wherein the phase of spins changes radially over the segment.

95. The apparatus of claim 93 wherein the phase of spins changes azimuthally over the segment.

96. The apparatus of claim 93 wherein the phase of spins changes axially over the segment.

97. The apparatus of claim 89 further comprising means for generating a sequence of pulses and spin-echoes which provide an azimuthally resolved nuclear magnetic resonance measurement.

98. The apparatus of claim 97 further comprising means for generating a first pulse sequence comprising a plurality of phase alternated RF pulses a nd spin-echoes and means for generating a second pulse sequence comprising a plurality of phase alternated RF pulses, at least one gradient pulse, and spin-echoes.

99. The apparatus of claim 97 further comprising means for generating a pulse sequence e comprising a plurality of phase alternated RF pulses, at least one gradient pulse, and spin-echoes.

100. The apparatus of claim 93 further comprising means for generating a sequence of pulses and spin-echoes which provide an azimuthally resolved nuclear magnetic resonance measurement.

101. The apparatus of claim 100 further comprising means for generating a first pulse sequence comprising a plurality of phase alternated RF pulses and spin-echoes and means for generating a second pulse sequence comprising a plurality of phase alternated RF pulses, at least one gradient pulse, and spin-echoes.

102. The apparatus of claim 100 further comprising means for generating a pulse sequence comprising a plurality of phase alternated RF pulses, at least one gradient pulse, and spin-echoes.

103. The apparatus of claim 88 wherein the magnetic gradient field has a polarization orientation in the investigation region substantially the same as the static magnetic field.

104. A method for measuring a nuclear magnetic resonance property in an investigation region of earth formations surrounding a borehole, comprising the steps of:
  a) positioning a logging device in the borehole;
  b) measuring the nuclear magnetic resonance property, comprising the steps of:
    i) applying a static magnetic field circumferentially around the borehole and into the investigation region;
    ii) applying an RF magnetic field circumferentially around the borehole;
    iii) inducing a plurality of spin-echo signals from selected nuclei of the formation;
    iv) applying a magnetic field gradient to dephase spins in a portion of the investigation region; and
    v) detecting nuclear magnetic resonance signals from the investigation region.

105. The method of claim 104 further comprising the steps of partitioning a cross-section of the formation into a plurality of angular distance segments around the borehole and altering the phase of spins in at least one segment by spatially varying the static magnetic field strength so that a net magnetization within the segment is zero.

106. The method of claim 105 further comprising the step of radially changing the phase of spins within the segment.

107. The method of claim 105 further comprising the step of azimuthally changing the phase of spins within the segment.

108. The method of claim 105 further comprising the step of axially changing the phase of spins within the segment.

109. The method of claim 105 further comprising the step of generating a sequence of pulses and spin-echoes which provide an azimuthally resolved nuclear magnetic resonance measurement.

110. The method of claim 109 further comprising the step of generating a first pulse sequence comprising a plurality of phase alternated RF pulses and spin-echoes and generating a second pulse sequence comprising a plurality of phase alternated RF pulses, at least one gradient pulse, and spin echoes.

111. The method of claim 109 further comprising the step of generating a pulse sequence comprising a plurality of phase alternated RF pulses, at least one gradient pulse, and spin-echoes.

112. The method of claim 104 wherein the magnetic gradient field has a polarization orientation in the investigation region substantially the same as the static magnetic field.

113. The method of claim 109 wherein during a single pulse sequence, the step of generating a sequence of pulses and spin-echoes comprises the steps of:
  i) during a first time period, applying a first plurality of RF pulses and at least one gradient pulse in the investigation region and measuring the generated signals in the investigation region, the measured signals comprise a ringing component and spin-echoes;
  ii) canceling the spin-echoes;
  iii) during a second time period, applying a second plurality of RF pulses and at least one gradient pulse in the investigation region and measuring the generated signals in the investigation region, the measured signals comprise the ringing component and substantially exclude the spin-echoes; and,
  iv) correcting the signals measured during the first time period to eliminate the ringing component.

114. The method of claim 104 further comprising the steps of partitioning a cross-section of the formation into a plurality of angular distance segments around the borehole and altering the phase of spins in at least one segment by applying the gradient field substantially parallel to the static magnetic field so that a net magnetization over the segment is non-zero and has a different phase than the net magnetization in the remaining portion of the investigation region.

115. The method of claim 114 further comprising the step of radially changing the phase of spins within the segment.

116. The method of claim 114 further comprising the step of azimuthally changing the phase of spins within the segment.

117. The method of claim 114 further comprising the step of axially changing the phase of spins within the segment.

118. The method of claim 114 further comprising the step of generating a sequence of pulses and spin-echoes which provide an azimuthally resolved nuclear magnetic resonance measurement.

119. The method of claim 108 further comprising the step of generating a first pulse sequence comprising a plurality of phase alternated RF pulses and spin-echoes and generating a second pulse sequence comprising a plurality of phase alternated RF pulses, at least one gradient pulse, and spin echoes.

120. The method of claim 108 further comprising the step of generating a pulse sequence comprising a plurality of phase alternated RF pulses, at least one gradient pulse, and spin-echoes.

121. The method of claim 108 wherein during a single pulse sequence, the step of generating a sequence of pulses and spin-echoes comprises the steps of:
  i) during a first time period, applying a first plurality of RF pulses and at least one gradient pulse in the investigation region and measuring the generated signals in the investigation region, the measured signals comprise a ringing component and spin-echoes;
  ii) canceling the spin-echoes;
  iii) during a second time period, applying a second plurality of RF pulses and at least one gradient pulse in the investigation region and measuring the generated signals in the investigation region, the measured signals comprise the ringing component and substantially exclude the spin-echoes; and,
  iv) correcting the signals measured during the first time period to eliminate the ringing component.

122. An apparatus for determining a nuclear magnetic resonance property in an investigation region of earth formations surrounding a borehole, comprising:
  a) a logging device moveable through the borehole;
  b) means in the logging device for applying a static magnetic field into the investigation region;
  c) antenna means in the logging device for applying an RF magnetic field into the investigation region whereby the antenna means induces a plurality of spin-echo signals from selected nuclei of the formation;
  d) gradient means in the logging device for applying a magnetic field gradient to dephase spins in a portion of the investigation region; and e) means for detecting nuclear magnetic resonance signals from the investigation region.

123. The apparatus of claim 122 further comprising means for partitioning a cross-section of the formation into a plurality of angular distance segments around the borehole wherein the gradient means alters the phase of spins by spatially varying the static magnetic field strength in at least one segment so that a net magnetization over the segment is substantially zero.

124. The apparatus of claim 122 further comprising means for partitioning a cross-section of the formation into a plurality of angular distance segments around the borehole wherein the gradient means alters the phase of spins by spatially varying the static magnetic field strength in at least one segment so that a net magnetization over the segment is non-zero and has a different phase than the net magnetization in the remaining portion of the investigation region.

125. The apparatus of claim 122 further comprising means for partitioning a cross-section of the formation into at least one axial segment wherein the gradient means alters the phase of spins by spatially varying the static magnetic field strength in the segment so that a net magnetization over the segment is substantially zero.

126. The apparatus of claim 122 further comprising means for partitioning a cross-section of the formation into at least one axial segment wherein the gradient means alters the phase of spins by spatially varying the static magnetic field strength in the segment so that a net magnetization over the segment is non-zero and has a different phase than the net magnetization in the remaining portion of the investigation region.

127. The apparatus of claim 122, wherein the logging device is coupleable into a drill string.

128. A method for measuring a nuclear magnetic resonance property in an investigation region of earth formations surrounding a borehole, comprising:
  a) drilling a borehole into the formation;
  b) applying a static magnetic field into the investigation region;
  c) applying an RF magnetic field into the investigation region and inducing a plurality of spin-echo signals from selected nuclei of the formation;
  d) applying a magnetic field gradient to dephase spins in a portion of the investigation region; and
  e) detecting nuclear magnetic resonance signals from the investigation region.

129. The method of claim 128 further comprising the steps of partitioning a cross-section of the formation into a plurality of angular distance segments around the borehole and altering the phase of spins by spatially varying the static magnetic field strength in at least one segment so that a net magnetization over the segment is substantially zero.

130. The method of claim 128 further comprising the steps of partitioning a cross-section of the formation into a plurality of angular distance segments around the borehole and altering the phase of spins by spatially varying the static magnetic field strength in at least one segment so that a net magnetization over the segment is non-zero and has a different phase than the net magnetization in the remaining portion of the investigation region.

131. The method of claim 128 further comprising the steps of partitioning a cross-section of the formation into at least one axial segment and altering the phase of spins by spatially varying the static magnetic field strength in the segment so that a net magnetization over the segment is substantially zero.

132. The method of claim 128 further comprising the steps of partitioning a cross-section of the formation into at least one axial segment and altering the phase of spins by spatially varying the static magnetic field strength in the segment so that a net magnetization over the segment is non-zero and has a different phase than the net magnetization in the remaining portion of the investigation region.

133. The method of claim 128 further comprising the step of measuring the nuclear magnetic resonance property while drilling into the formation.

134. The apparatus of claim 122 further comprising means for partitioning a cross-section of the formation into at least one radial segment wherein the gradient means eliminates the magnetic resonance signal of the borehole fluids.

135. The apparatus of claim 122 further comprising a pad connected to the logging device and adapted to be pressed against the borehole wall, the pad carrying at least one of the gradient means located to face the borehole wall.

136. The apparatus of claim 126 further comprising means for enhancing vertical resolution of the detected signals.

137. The method of claim 16 further comprising the steps of providing a plurality of gradient means positioned around the circumference of the logging device and selecting at least one of the gradient means to apply the magnetic field gradient.

138. The method of claim 128 further comprising the steps of mapping the signals to an angular or axial position to produce an image of the formation.

139. The apparatus of claim 9 wherein the gradient means comprises a single coil.

* * * * *